United States Patent
Friedman et al.

(10) Patent No.: US 7,678,888 B2
(45) Date of Patent: Mar. 16, 2010

(54) STABLE OXIDATION RESISTANT POWDERED HEMOGLOBIN, METHODS OF PREPARING SAME, AND USES THEREOF

(75) Inventors: Joel M. Friedman, South Orange, NJ (US); Mahantesh S. Navati, Bronx, NY (US)

(73) Assignee: Albert Einstein College of Medicine of Yeshiva University, Bronx, NY (US)

( * ) Notice: Subject to any disclaimer, the term of this patent is extended or adjusted under 35 U.S.C. 154(b) by 146 days.

(21) Appl. No.: 10/593,387

(22) PCT Filed: Apr. 20, 2005

(86) PCT No.: PCT/US2005/013222

§ 371 (c)(1),
(2), (4) Date: Aug. 14, 2007

(87) PCT Pub. No.: WO2005/103080

PCT Pub. Date: Nov. 3, 2005

(65) Prior Publication Data

US 2008/0039370 A1     Feb. 14, 2008

Related U.S. Application Data

(60) Provisional application No. 60/564,166, filed on Apr. 21, 2004.

(51) Int. Cl.
*C07K 14/00* (2006.01)
(52) U.S. Cl. .................................................. 530/385
(58) Field of Classification Search ........................ None
See application file for complete search history.

(56) References Cited

U.S. PATENT DOCUMENTS

| | | | |
|---|---|---|---|
| 3,964,865 A * | 6/1976 | Das .............................. | 436/66 |
| 4,377,512 A * | 3/1983 | Ajisaka et al. .............. | 530/385 |
| 4,425,334 A | 1/1984 | Hunt | |
| 5,079,337 A | 1/1992 | Leonard et al. | |
| 5,110,909 A | 5/1992 | Dellacherie et al. | |
| 5,234,903 A | 8/1993 | Nho et al. | |
| 5,498,421 A | 3/1996 | Grinstaff et al. | |
| 5,635,207 A | 6/1997 | Grinstaff et al. | |
| 5,639,473 A | 6/1997 | Grinstaff et al. | |
| 6,747,132 B2 * | 6/2004 | Privalle et al. .............. | 530/385 |
| 2002/0099175 A1 | 7/2002 | Privalle et al. | |

FOREIGN PATENT DOCUMENTS

| | | | |
|---|---|---|---|
| WO | 03/045163 | * | 6/2003 |
| WO | WO 2007/100609 A2 | | 9/2007 |
| WO | WO 2007/149520 A2 | | 12/2007 |

OTHER PUBLICATIONS

Heller et al., entitled "Conformational Stability of Lyophilized PEGylated Proteins in a Phase-Separating System," Journal of Pharmaceutical Sciences, Jan. 1999, vol. 88, No. 1, pp. 58-64.

Navati M S et al., entitled "Sugar-derived Glasses Support Thermal and Photo-initiated Electron Transfer Processes over Macroscoopic Distances," The Journal of Biological Chemistry, vol. 281, No. 47, pp. 36021-36028, Nov. 24, 2006.

Heller M C et al., entitled Protein Formulation and Lyophilization Cycle Design: Prevention of Damage Due to Freeze-Concentration Induced Phase Separation, Biotechnol Bioeng 63: 166-174, 1999.

Heller M C et al., entitled Application of a Thermodynamic Model to the Prediction of Phase Separations in Freeze-Concentrated Formulations for Protein Lyophilization, Archives of Biochemistry and Biophysics, vol. 363, No. 2, Mar. 15, pp. 191-201, 1999.

Heller M C et al, entitled "Manipulation of Lyophilization-Induced Phase Separation: Implications for Pharmaceutical Proteins," Biotechnol. Prog., 1997, 13, 590-596.

Heller M C et al., entitled "Effects of Phase Separating Systems on Lyophilized Hemoglobin," Journal of Pharmaceutical Sciences, vol. 85, No. 12, Dec. 1996, 1358-1362.

Ray A et al., entitled "Trehalose Glass-Facilitated Thermal Reduction of Metmyoglobin and Methemoglobin," J. Am. Chem. Soc. 2002, 124, 7270-7271.

\* cited by examiner

*Primary Examiner*—Karen Cochrane Carlson
(74) *Attorney, Agent, or Firm*—Amster, Rothstein & Ebenstein LLP

(57) ABSTRACT

The present invention provides oxygenated hemoglobins in powdered form and methods of preparing a powdered form of a protein, such as hemoglobin, which comprise (a) mixing a solution of the protein with inulin, and optimally with a reducing sugar such as glucose or tagatose, and (b) drying the mixture. Also provided are blood substitutes formed from reconstituted powdered hemoglobins, and methods of treatment using the blood substitutes.

16 Claims, No Drawings

STABLE OXIDATION RESISTANT POWDERED HEMOGLOBIN, METHODS OF PREPARING SAME, AND USES THEREOF

CROSS-REFERENCE TO RELATED APPLICATION

This application is a national stage entry under 35 U.S.C. §371 of PCT International Patent Application No. PCT/US2005/013222, filed Apr. 20, 2005, which claims the benefit of U.S. Provisional Patent Application No. 60/564,166, filed on Apr. 21, 2004, the contents of which are hereby incorporated by reference into the subject application.

STATEMENT OF GOVERNMENT SUPPORT

This invention was made with United States government support under grant numbers HL-71064 and EB-00296 from the National Institutes of Health and a grant from the U.S. Army. Accordingly, the United States government has certain rights in this invention.

BACKGROUND OF THE INVENTION

Surgery and trauma conditions often require blood transfusion. Blood substitutes are needed for use in emergency transfusions under conditions of extreme blood loss. PEGylated hemoglobins are hemoglobins that that have been chemically modified through the attachment of polyethyleneglycol (PEG) to the protein. The mode of attachment, the site(s) of attachment, and the size and number of attached PEG chains can be varied (e.g., U.S. Pat. Nos. 5,585,484, 5,750,725, and 6,017,943; U.S. Patent Application Publication Nos. 2003/0187248 A1 and 2004/0002443 A1). PEGylated hemoglobins show ever increasing promise as blood substitutes for emergency use. An important issue, both economic and clinical, is the development of protocols to store these materials for long periods without loss of efficacy. This point is especially significant since the production, transportation and storage costs for these materials are likely to be high. The production of a reconstitutable powdered form of a blood substitute that allows for long term storage and facile transport at ambient temperatures would significantly reduce costs and increase the clinical applicability of these materials under emergency and combat situations.

Long term storage of hemoglobins is typically complicated by autoxidation (formation of methemoglobin), whereby the ferrous (reduced) oxygen carrying form of the protein converts to the ferric (oxidized) non-oxygen transporting form referred to as methemoglobin. In addition to being ineffective as an oxygen carrier, the met form of hemoglobin has an increased tendency to release the heme portion of hemoglobin. The heme is toxic when free of the protein.

Liquid forms of hemoglobin including PEGylated hemoglobins can be prepared and stored for long periods at cryogenic temperatures with minimal formation of met hemoglobin. The downside to this approach is the cost of maintaining the product at cryogenic temperatures, the cost of shipping the inherently heavy solutions (frozen or liquid) and the ability to maintain these samples for extended periods in emergency vehicles especially under combat conditions. Far more preferable would be a dry stable (with respect to methemoglobin formation) light-weight product that can be stored at higher temperatures, transported for long stretches without the need for ongoing refrigeration and easily reconstituted in the field.

There are two commonly used methods for producing powdered forms of protein. The more routine approach is freeze-drying or lyophilization. Lyophilization protocols consist of first freezing the liquid sample and then drying it under a vacuum to remove water. The other approach, based on air drying, utilizes a special nozzle technology to produce a high speed jet of material that forms easily dried micro-droplets.

Successful lyophilization requires that proteins survive both the freezing and drying phases of the process. Many proteins including hemoglobin undergo some degree of denaturation when lyophilized from an aqueous solution. The addition of simple (non-reducing) sugars especially glass forming sugars such as trehalose has been shown to greatly limit protein damage during lyophilization. Unfortunately, the combination of trehalose and PEG typically results in phase separation and loss of protection during lyophilization. Furthermore, lyophilization of oxygenated derivatives of PEGylated hemoglobins using trehalose results in dried material almost completely in the met form. The met formation also occurs when trehalose-containing samples of PEGylated oxygenated hemoglobin are allowed to air dry without resorting to lyophilization.

SUMMARY OF THE INVENTION

The present invention provides an oxygenated hemoglobin in powdered form, which is resistant to oxidation and stable at room temperature.

The present invention also provides a method of preparing a powdered form of a protein, such as hemoglobin, which comprises (a) mixing a solution of the protein with inulin, and optimally with a reducing sugar such as glucose or tagatose, and (b) drying the mixture. Also provided are powdered hemoglobins, and blood substitutes formed from reconstituted powdered hemoglobins, and methods of treatment using the blood substitutes.

Additional objects of the invention will be apparent from the description which follows.

DETAILED DESCRIPTION OF THE INVENTION

The present invention is directed to an oxygenated hemoglobin in powdered form. Preferably, the hemoglobin is resistant to oxidation and is stable at room temperature. The hemoglobin can be a pegylated hemoglobin. Also provided is a composition of powdered hemoglobin comprising oxygenated hemoglobin and no more than 20% of the met form of hemoglobin. Preferably, the composition comprises no more than 10% of the met form of hemoglobin. More preferably, the composition comprises no more than 5% of the met form of hemoglobin.

The present invention also provides a method of preparing a powdered form of a protein, which comprises: (a) mixing a solution of the protein with inulin, and (b) drying the mixture. Also provided is a method of preparing a powdered form of a protein, which comprises: (a) mixing a solution of the protein with inulin and with a reducing sugar, and (b) drying the mixture. Preferably, the inulin is derived from Chicory Root. The reducing sugar can be, for example, glucose and/or tagatose, and is preferably tagatose. The drying step can comprise lyophilization and/or air drying. In one embodiment, the mixture is cooled as it is being air dried.

The methods described herein can be used to prepare a powdered form of hemoglobin. The hemoglobin can be pegylated. Preferably, the hemoglobin is oxygenated. The invention also provides a powdered hemoglobin prepared by any of the methods disclosed herein. Preferably, the powdered hemoglobin contains no more than 20% of the met form of hemoglobin, more preferably no more than 10% of the met form of hemoglobin, and most preferably no more than 5% of the met form of hemoglobin.

Also provided is a method of preparing a blood substitute which comprises reconstituting any of the powdered hemoglobins described herein. The powdered hemoglobins can be reconstituted by a method which comprises dissolving the powdered hemoglobin in an aqueous buffer solution. The method can comprise cooling the buffer and/or aerating the buffer. The invention also provides a blood substitute prepared by any of the methods disclosed herein. Preferably, the hemoglobin in the blood substitute comprises no more than 20% of the met form of hemoglobin, more preferably no more than 10% of the met form of hemoglobin, and most preferably no more than 5% of the met form of hemoglobin.

The hemoglobins described herein, including the hemoglobins used in any of the methods, compositions, and blood substitutes described herein, can be pegylated hemoglobins. The pegylated hemoglobin can comprise one or more polyethylene glycol (PEG) molecules with a molecular weight of 200-40,000 daltons. The pegylated hemoglobin can be pegylated, for example, using 2-8 PEGs or 2-4 PEGs. The PEGs can comprise a PEG with a molecular weight of 5,000 daltons. PEGs of various molecular weights, conjugated to various groups, can be obtained commercially, for example from Nektar Therapeutics AL, Corporation, Huntsville, Ala.

Pharmaceutically acceptable carriers that can be used in blood substitutes include, but are not limited to, saline, phosphate buffered saline, Ringer's solution, lactated Ringer's solution, Locke-Ringer's solution, Kreb's Ringer's solution, Hartmann's balanced saline solution, Bis tris acetate buffer, phosphate buffer and heparinized sodium citrate acid dextrose solution. The pharmaceutical compositions also may comprise known plasma substitutes and plasma expanders. The pharmaceutical compositions of the present invention may be used as blood substitutes, and the like, and may be administered by conventional means including but not limited to transfusion and injection.

The invention provides a method of treating a subject which comprises administering to the subject any of the blood substitutes disclosed herein or prepared using any of the methods disclosed herein. Also provided is a method of treating a subject which comprises reconstituting any of the powdered hemoglobins disclosed herein, and administering the reconstituted hemoglobin to the subject. The subject may have a blood loss due to a surgical procedure or to a wound. Prior to treatment, the subject may have a reduced red blood cell count or a reduced blood volume. The subject may have a disease characterized by vaso-occlusion or impaired blood flow. Such diseases include, but are not limited to, sickle cell disease, myocardial infarction and/or shock.

The present invention is illustrated in the following Experimental Details section, which is set forth to aid in the understanding of the invention, and should not be construed to limit in any way the scope of the invention as defined in the claims that follow thereafter.

Experimental Details

I. Overview

In addressing the challenge of protocols for long term storage of hemoglobin, one is confronted with several issues. It is possible to store ferrous forms (the active form) of hemoglobin either as the deoxygenated (deoxy) derivative or the oxygenated (oxy) derivative. The deoxy derivative is typically much more stable but is costly to prepare in that large volumes of material must be prepared and stored under oxygen-free conditions. From a practical economic perspective, the oxy derivative is preferable but is much more prone to autoxidation.

For a storage protocol based on the more economically desirable approach using oxygenated hemoglobins, autoxidation must be controlled. Autoxidation, i.e. the formation of methemoglobin from the starting oxygenated hemoglobin, occurs largely through a process that necessitates the rupture of the bond between the iron and the bound oxygen. The spontaneous dissociation of the oxygen from the iron is driven by heat induced fluctuations in the structure of the hemoglobin that cause the transient stretching of the bond between the iron and the bound oxygen. Thus, rupture of the bond is greatly reduced when the oxygenated hemoglobin is in an environment that reduces or eliminates the heat driven fluctuations that drive the dissociation process. It follows that a key aspect in a storage protocol for oxygenated hemoglobins entails a storage medium or environment that limits these structural fluctuations. This limiting of structural fluctuations can be achieved either through cryogenic storage of solutions or through the incorporation of the hemoglobin into suitable solid matrices that restrict protein motions even at elevated temperatures.

Appropriate solid matrices are glassy matrices derived from sugars or starches. Sample preparation requires dissolving the appropriate amount of the sugar or carbohydrate into the solution of protein and then drying the sample in a manner that leads to the formation of a rigid glassy matrix. Proteins incorporated into these sugar-glasses can have greatly reduced motions depending on the nature of the protein and the sugar used. The inclusion of reducing sugars within glassy matrices has been shown to facilitate reduction of met hemoglobin (Ray et al., 2002).

II. Methods and Materials

Stock solutions of inulin with (10 mg/ml) and without added reducing sugars (glucose or tagatose) are prepared using 29 mg/ml of Chicory Root inulin purchased commercially from Sigma dissolved in distilled water. The inulin stock solution is combined with an equal volume of buffered (either 50 mM Bis tris acetate, pH 7.0 or 10 mM phosphate pH 7.4) hemoglobin solution (40 mg/ml). Two different hemoglobins have been used: human adult hemoglobin (HbA) and HbA modified with the covalent attachment of 6 PEG5000 chains (HbP5K6). The resulting solution is then subjected to either of two protocols: lyophilization or air drying.

Lyophilization is carried out in a commercial instrument. In this protocol the solution is first frozen in liquid nitrogen and then subjected to a vacuum to dry the sample. The resulting powder is then stored in a sealed vial at ambient conditions.

The air drying protocol entails pouring the above solution onto a glass plate and drying the thin layer of solution in a dry box (an airtight box that contains a drying agent) sealed under ambient conditions. The sample typically takes one day to form a dry glassy matrix that flakes into a powder when scraped into a vial for storage.

Reconstituted hemoglobin solutions derived from the powder are generated by dissolving the powder in a suitable aqueous buffer solution (e.g. Bis tris acetate or phosphate). The efficacy of the protocol is evaluated by calculating from the absorption spectrum (using a well established formula) the amount of oxygenated hemoglobin and met hemoglobin present in the reconstituted solution.

III. Results

Drying oxygenated hemoglobin without the addition of glass-forming sugars or starches results in the formation of very large amounts of methemoglobin. Thus, either lyophilization or air drying protocols require the use of glass forming materials that will protect and stabilize the oxygenated hemoglobin both during and after drying.

Inulin containing samples form a very fine powder when either lyophilized or air dried. Both protocols yield a fine powder that shows no obvious external signs of change when stored in a sealed vial over a period of months. This powder is easily redissolved in water. Most significantly the amount of met formation is markedly reduced when inulin is used.

Several different inulins were tried. Commercially available (from Sigma) inulin derived from Chicory Root gave the best results.

The use of inulin as the glass forming additive to either the lyophilization or air-drying protocols significantly reduces the amount of met hemoglobin formed but does not completely eliminate met formation. The yield of met hemoglobin varies inversely with the relative concentration of added inulin. For a given relative concentration, the air dried protocols yield less met hemoglobin than the lyophilization protocols.

To further reduce the amount of met hemoglobin being formed during either drying process, either the sugar glucose or tagatose was added to the starting inulin-containing solution. The inclusion of either glucose or tagatose to the inulin-based protocol for air or freeze drying, results in further reduction in met formation compared to the inulin-alone protocols. Tagatose is more effective than glucose in reducing the amount of met hemoglobin formed during drying. Tagatose also has the added advantages that it does not appear to glycosylate proteins, which is a problem associated with glucose, and that it confers protection against iron-related oxidative damage.

Further reductions in the amount of formed methemoglobin can be achieved by cooling the sample as it is being air dried and using cooled aerated buffer for the reconstitution phase.

IV. Discussion

The present application describes the use of inulin, and optimally a reducing sugar such as tagatose or glucose, for preparing dry powdered forms of oxygenated hemoglobins, including PEGylated hemoglobins. The naturally occurring starch inulin has a very high glass transition temperature of close to 100° C. This high glass transition temperature indicates that the proteins incorporated into inulin-derived glasses will likely remain stable even when the glass is heated close to the boiling point of water. Inulin is used clinically in an infusible form to measure internal volumes.

Studies have been conducted using both lyophilization and air drying. Commercial air drying devices are suited for very large volumes of material. The air drying experiments described herein, conducted on small volumes of sample, utilize methodologies that circumvent the unavailability of a suitable commercial air drying instrument. It is anticipated that the air drying approach will be the method of choice based on both the economics of producing large amounts of dried material and the experimental results described herein.

The PEGylated hemoglobin used in this study has six copies of PEG5000 attached. It represents an extreme with respect to PEG modifications. Hemoglobins with either 4 or even two copies of PEG may be suitable as a blood substitute and should be more stable in powder form than the hemoglobin with six PEG copies. The protocol described herein is anticipated to be valid for generating powdered forms of a range of modified hemoglobins ranging from those with no attached PEG up to those with the maximum number of attached PEGs (6-8 PEGs).

All publications mentioned herein are hereby incorporated in their entirety into the subject application. While the foregoing invention has been described in some detail for purposes of clarity and understanding, it will be appreciated by one skilled in the art, from a reading of the disclosure, that various changes in form and detail can be made without departing from the true scope of the invention in the appended claims.

REFERENCES

Ray, A., Friedman, B.A., Friedman, J.M. Trehalose glass-facilitated thermal reduction of metmyoglobin and methemoglobin. J. Am. Chem. Soc. 124(25): 7270-1, 2002.

U.S. Pat. No. 5,585,484, Hemoglobin Crosslinkers, Acharya et al., issued Dec. 17, 1996.

U.S. Pat. No. 5,750,725, Hemoglobin Crosslinkers, Acharya et al., issued May 12, 1998.

U.S. Pat. No. 6,017,943, Hemoglobin Crosslinkers, Acharya et al., issued Jan. 25, 2000.

U.S. Patent Application Publication No. 2003/0187248 A1, Smith, Activated Polyethylene Glycol Compounds, published Oct. 2, 2003.

U.S. Patent Application Publication No. 2004/0002443 A1, Acharya et al., Size Enhanced Hemoglobins: Surface Decoration and Crosslinking of the Protein with Polyoxy Alkylene Glycols, published Jan. 1, 2004.

What is claimed is:

1. A method of preparing a powdered form of a protein, which comprises:
   (a) mixing a solution of the protein with inulin and tagatose, and
   (b) drying the mixture.

2. The method of claim 1, wherein the inulin is derived from Chicory Root.

3. The method of claim 1, wherein the drying step comprises lyophilization.

4. The method of claim 1, wherein the drying step comprises air drying.

5. The method of claim 4, wherein the mixture is cooled as it is being air dried.

6. The method of claim 1, wherein the protein is hemoglobin.

7. The method of claim 6, wherein the hemoglobin is pegylated.

8. The method of claim 7, wherein the pegylated hemoglobin comprises one or more polyethylene glycol (PEG) molecules with a molecular weight of 200-40,000 daltons.

9. The method of claim 8, wherein the PEGs comprise a PEG with a molecular weight of 5,000 daltons.

10. The method of claim 7, wherein the hemoglobin is pegylated with 2-8 PEGs.

11. The method of claim 7, wherein the hemoglobin is pegylated with 2-4 PEGs.

12. The method of claim 6, wherein the hemoglobin is oxygenated.

13. The method of claim 12, wherein the hemoglobin is resistant to oxidation.

14. The method of claim 12, wherein the hemoglobin is stable at room temperature.

15. The method of claim 12, wherein the powdered hemoglobin contains no more than 20% of the met form of hemoglobin.

16. The method of claim 12, wherein the powdered hemoglobin contains no more than 10% of the met form of hemoglobin.

* * * * *